United States Patent [19]

Hattori et al.

[11] Patent Number: 5,478,789
[45] Date of Patent: Dec. 26, 1995

[54] HYDROGENATION REACTION CATALYST PRECURSOR, PROCESS FOR PRODUCTION THEREOF AND PROCESS FOR PRODUCTION OF ALCOHOL

[75] Inventors: Yasuyuki Hattori; Kiyoshi Tsukada, both of Wakayama, Japan

[73] Assignee: Kao Corporation, Tokyo, Japan

[21] Appl. No.: 317,368

[22] Filed: Oct. 4, 1994

[30] Foreign Application Priority Data

Oct. 4, 1993 [JP] Japan .................................. 5-273189

[51] Int. Cl.$^6$ ........................ B01J 21/06; B01J 23/72; C07C 27/04
[52] U.S. Cl. .................... 502/244; 502/250; 502/263; 502/342; 502/346; 502/351; 502/355; 568/885; 568/811; 568/814; 568/864
[58] Field of Search .................................. 502/244, 342, 502/346, 355, 351, 250, 263; 568/885, 811, 814, 864

[56] References Cited

U.S. PATENT DOCUMENTS

| | | | |
|---|---|---|---|
| 4,039,478 | 8/1977 | Cull et al. ......................... | 252/455 R |
| 4,918,248 | 4/1990 | Hattori et al. ...................... | 568/885 |
| 4,920,088 | 4/1990 | Kolts ................................ | 502/326 |
| 4,929,777 | 5/1990 | Irick, Jr. et al. .................. | 568/864 |
| 5,229,346 | 7/1993 | Mori et al. ........................ | 502/302 |

FOREIGN PATENT DOCUMENTS

| | | |
|---|---|---|
| 345695 | 12/1989 | European Pat. Off. . |
| 1305042 | 12/1989 | Japan . |
| 3220143 | 9/1991 | Japan . |

*Primary Examiner*—Asok Pal
*Assistant Examiner*—Timothy H. Meeks
*Attorney, Agent, or Firm*—Birch, Stewart, Kolasch & Birch

[57] ABSTRACT

A hydrogenation reaction catalyst precursor of the present invention comprises a catalyst carrier (A) and a metal oxide composition (B) carried on or mixed with the catalyst carrier (A) at a weight ratio of (B)/(A)=15/85 to 65/35; the catalyst carrier (A) comprising a carrier base material of silica, etc. and a coating of titanium oxide and/or titanium hydroxide, the metal oxide composition (B) comprising copper oxide, zinc oxide, and at least one oxide of a metal selected from the group consisting of an element of group IIa of the periodic table, an element of group IIIb of the table, a lanthanide element, and an actinide element at a weight ratio of 100/(0 to 25)/(0 to 25). A hydrogenation reaction catalyst with a high catalytic activity and a high reaction selectivity is obtained by reduction of the hydrogenation reaction catalyst precursor. By the use of the hydrogenation reaction catalyst of the present invention, a high quality alcohol can be produced at a high yield and with a high selectivity even at a low reaction temperature and a low hydrogen pressure.

15 Claims, No Drawings

HYDROGENATION REACTION CATALYST PRECURSOR, PROCESS FOR PRODUCTION THEREOF AND PROCESS FOR PRODUCTION OF ALCOHOL

BACKGROUND OF THE INVENTION

1. Field of the Invention

The present invention relates to a hydrogenation reaction catalyst precursor, to a process for production thereof, to a hydrogenation reaction catalyst, and to a process for producing an alcohol using the hydrogenation reaction catalyst.

2. Discussion of the Related Art

In Japanese Unexamined Patent Publication Nos. 1-305042 and 5-177140 (corresponding U.S. Pat. Nos. are 4,918,248 and 5,229,346, respectively), there is disclosed a process for producing an alcohol utilizing a copper-zinc hydrogenation reaction catalyst precursor having a copper-zinc catalytic component carried on a titanium oxide and/or titanium hydroxide carrier base material. The copper-zinc catalyst precursor undergoes reductive activation and exhibits a high catalytic activity and a high reaction selectivity in alcohol production.

However, the titanium oxide and/or titanium hydroxide carrier base material of the catalyst precursors disclosed in the above publications, e.g., a commercially available titanium oxide which has a large surface area and a titanium oxide and/or titanium hydroxide which is obtained by hydrolysis of an alkoxide of titanium, are expensive as compared with ordinary carrier materials such as silica, alumina, silica-alumina, and zeolite. Therefore, the catalyst precursor using the titanium oxide and/or titanium hydroxide as a carrier base material has a problem of a high production cost. In addition, for further enhancement of the economical efficiency of alcohol production on an industrial scale, further improvement in catalytic activity and reaction selectivity has been sought.

On the other hand, a hydrogenation reaction catalyst using a less expensive carrier base material such as silica, alumina, and zeolite, instead of titanium oxide and/or titanium hydroxide, seemed to be significantly inferior to those using titanium oxide and/or titanium hydroxide in catalytic activity and reaction selectivity. Therefore, it has generally been thought that a catalyst using a material other than titanium oxide and/or titanium hydroxide as a carrier base material cannot practically be employed for alcohol production.

SUMMARY OF THE INVENTION

Accordingly, an object of the present invention is to provide a hydrogenation reaction catalyst precursor which exhibits a high catalytic activity and a high reaction selectivity and which can be produced at a low cost.

A further object of the present invention is to provide a process for producing the hydrogenation reaction catalyst precursor.

A still further object of the present invention is to provide a hydrogenation reaction catalyst by reductive activation of the hydrogenation reaction catalyst precursor.

Another object of the present invention is to provide a process for efficiently and economically producing an alcohol of high quality using the above-mentioned hydrogenation reaction catalyst.

As the result of various investigations to achieve the above objects, the inventors have found that a certain process makes it possible to produce a hydrogenation reaction catalyst precursor which, even though a less expensive material than titanium oxide is used as a carrier base material, exhibits an unexpectedly high catalytic activity and reaction selectivity after it is activated.

Specifically, the gist of the present invention relates to:

(1) A hydrogenation reaction catalyst precursor comprising a catalyst carrier (A) and a metal oxide composition (B) carried on or mixed with the catalyst carrier (A) at a weight ratio of (B)/(A)=15/85 to 65/35, wherein the catalyst carrier (A) comprises a carrier base material of at least one kind selected from the group consisting of silica, alumina, silica-alumina, magnesia, zirconia, zeolite, and diatomaceous earth, and a titanium oxide and/or titanium hydroxide, the carrier base material being coated with the titanium oxide and/or titanium hydroxide; and wherein the metal oxide composition (B) comprises copper oxide, zinc oxide, and at least one oxide of a metal selected from the group consisting of an element of group IIa of the periodic table, an element of group IIIb of the periodic table, a lanthanide element, and an actinide element at a weight ratio of 100/(0 to 25)/(0 to 25);

(2) A process for producing the hydrogenation reaction catalyst precursor, comprising the steps of:

(i) coating a surface of the carrier base material with the titanium oxide and/or titanium hydroxide formed by hydrolyzing at least one of a titanium alkoxide represented by the following Formula (I) and a titanium alkoxo acid represented by the following Formula (II) to obtain a catalyst carrier (A):

$$Ti(OR)_4 \qquad (I)$$

wherein R represents an alkyl group having from 1 to 18 carbon atoms or aryl group, and

$$H_2[Ti(OR)_6] \qquad (II)$$

wherein R has the same meaning as above; and (ii) applying the metal oxide composition (B) onto the catalyst carrier (A) obtained in step (i) or mixing the metal oxide composition (B) with the catalyst carrier (A) at a weight ratio of (B)/(A)=15/85 to 65/35 to obtain a hydrogenation reaction catalyst precursor, wherein the catalyst carrier (A) may be or may not be calcinated in advance;

(3) The hydrogenation reaction catalyst obtained by reducing the hydrogenation reaction catalyst precursor described in (1); and (4) A process for producing an alcohol, wherein an organic carboxylic acid ester is catalytically hydrogenated with hydrogen in the presence of the hydrogenation reaction catalyst described in (3).

By the use of the hydrogenation reaction catalyst of the present invention, an organic carboxylic acid ester can be catalytically hydrogenated with hydrogen at a practical reaction rate to produce a high quality alcohol at a high yield and with a high selectivity even at a low reaction temperature and a low hydrogen pressure. Moreover, the hydrogenation reaction catalyst of the present invention can be produced at a much lower cost than those using titanium oxide and/or titanium hydroxide as a carrier base material, and exhibits a higher catalytic activity and a higher reaction selectivity.

DETAILED DESCRIPTION OF THE INVENTION

The invention will be described in detail below along the steps in the present invention.

1. Preparation of the Catalyst Precursor
Step (i)

As a carrier base material, at least one kind selected from the group consisting of silica, alumina, silica-alumina, magnesia, zirconia, zeolite, and diatomaceous earth is used. The carrier base materials used in the present invention can be those which are commercially available, and there is no restriction on the process for producing these carrier base materials. The silica, alumina, magnesia or zirconia used in the present invention may be an oxide, a hydrate like a hydrogel or a hydroxide.

The silica-alumina may be of either natural or synthetic type. Examples of the natural-type silica-alumina include clay minerals such as montmorillonite, kaolinite and illite. Acid clay and its acid-treated product, activated acid clay, are also included in the examples of the natural type silica-alumina used in the present invention. The silica-alumina of synthetic type used in the present invention includes those which are synthesized, for example, from water glass, sulfuric acid, sodium aluminate and aluminum sulfate, and contain $SiO_2$ and $Al_2O_3$ in various proportions.

The zeolite used in the present invention is water-containing crystalline alumino silicates which contain univalent and divalent cations. The typical examples include zeolites of type A, type L, mordenite type, type X and type Y.

The above carrier base materials may be used singly, as a mixture of two or more of them, or as a mixed metal compound.

The surface area of the carrier base material used in the present invention is an important factor for determining the catalytic activity. For activity in the hydrogenation reaction, the surface area of the carrier base material is preferably not less than 15 $m^2/g$, and more preferably in the range of from 50 $m^2/g$ to 1000 $m^2/g$. The surface area of less than 15 $m^2/g$ may cause insufficient catalytic activity. In this specification, the surface area refers to that measured by the BET method.

In the present invention, the carrier base material is coated with titanium oxide and/or titanium hydroxide by the method as mentioned below to give a catalyst carrier (A). If a hydrogenation reaction catalyst precursor is prepared using the above-mentioned carrier base materials without coating with titanium oxide and/or titanium hydroxide, the resulting catalyst precursor does not suit for practical alcohol production because its catalytic activity and reaction selectivity are significantly low (See Comparative Example 1).

Specifically, the surface of the above-mentioned carrier base material is coated with a titanium oxide and/or titanium hydroxide (hereinafter simply referred to as the coating titanium oxide/hydroxide) formed by hydrolyzing at least one of a titanium alkoxide having the above Formula (I) and a titanium alkoxo acid having the above Formula (II). In the formulas, R represents an alkyl group having from 1 to 18, preferably from 1 to 10 carbon atoms or an aryl group. Specifically, R may be a methyl group, an ethyl group, a propyl group, a butyl group, a pentyl group, a phenyl group or a naphthyl group.

By coating the carrier base material with the coating titanium oxide/hydroxide, the catalytic activity and reaction selectivity in a hydrogenation reaction is significantly improved as compared with the carrier base material without the coating treatment. Moreover, by the use of the above-mentioned carrier base materials, the catalytic activity and reaction selectivity of the resulting catalyst precursor becomes even higher than the catalyst precursor proposed by the inventors in Japanese Unexamined Patent Publication No. 5-177140 (U.S. Pat. No. 5,229,346) where titanium oxide ($TiO_2$) is used as a carrier base material. This may be explained by the effect of complex oxide formation between the coating titanium oxide/hydroxide and the carrier base material used in the present invention.

The weight ratio of the coating titanium oxide/hydroxide to the carrier base material is preferably from 5/100 to 100/100, more preferably from 5/100 to 50/100, particularly preferably from 5/100 to 30/100. If the amount of the coating titanium oxide/hydroxide is lower than 5/100, insufficient coating may result in lowering of catalytic activity and reaction selectivity in a hydrogenation reaction. On the other hand, if the amount of the coating titanium oxide/hydroxide is higher than 100/100, the obtained catalyst carrier is undesirable from the economical view point, though there is no problem in the catalytic performance.

Suitable processes for coating the carrier base material with the titanium oxide/hydroxide include a process of hydrolyzing titanium alkoxide having the above Formula (I) and/or titanium alkoxo acid having the above Formula (II) in the presence of the carrier base material to precipitate the titanium oxide/hydroxide on the surface of the carrier base material; and a process of blowing titanium alkoxide and/or titanium alkoxo acid onto the carrier base material and hydrolyzing the titanium compound by making it in contact with steam.

Step (ii)

In this step, a metal oxide composition (B), a catalytically active component, is applied onto or mixed with the catalyst carrier (A) prepared in step (i) to obtain a hydrogenation reaction catalyst precursor. Here, the catalyst carrier (A) may or may not be calcinated in advance.

When the metal oxide composition (B) is applied onto or mixed with the catalyst carrier (A), it is important to use them so that the weight ratio of the metal oxide composition (B) to the catalyst carrier (A) is in the range of from 15/85 to 65/35. When the ratio is within the range, the resulting hydrogenation reaction catalyst precursor can exhibit a high catalytic activity and a high reaction selectivity. If the amount of the catalyst carrier (A) exceeds the above range, the catalytically active metal oxide composition (B) is sparsely distributed on the surface of the catalyst carrier (A). This is economically disadvantageous because the utility efficiency of the surface area of the catalyst carrier (A) becomes low. If the amount of the catalyst carrier (A) is lower than the above range, the metal oxide composition (B) cannot effectively be applied onto the catalyst carrier (A), which impairs the aforementioned complex oxide effect and reduces the catalytic activity.

The metal oxide composition (B) comprises (a) copper oxide, (b) zinc oxide, and (c) at least one oxide of a metal selected from the group consisting of an element of group IIa of the periodic table, an element of group IIIb of the periodic table, a lanthanide element, and an actinide element at a weight ratio of 100/(0 to 25)/(0 to 25), preferably 100/(1 to 20)/(1 to 20).

If the weight ratio is not within the above range, the advantageous effects of the present invention cannot be obtained. If the amount of (b) exceeds 25 parts by weight, based on 100 parts by weight of (a), lowering of catalytic activity results. In order to enhance the catalytic activity, the metal oxide composition (B) should preferably contain (b) in an amount of 1 part by weight or more, based on 100 parts by weight of (a).

If the amount of (c) exceeds 25 parts by weight, based on 100 parts by weight of (a), the catalytic activity of the resulting catalyst becomes low, although the selectivity is sufficient. In order to enhance the selectivity, the metal oxide composition (B) should preferably contain (c) in an amount of 1 part by weight or more.

For use in the present invention, the elements of group IIa include Be, Mg, Ca, Sr, Ba, and Ra; the elements of group IIIb, Sc and Y; the lanthanide elements, La, Ce, Pr, Nd, Pm, Sm, Eu, Gd, Tb, Dy, Ho, Er, Tm, Yb, and Lu; and the actinide elements, Ac, Th, Pa, U, Np, Pu, Am, Cm, Bk, Cf, Es, Fm, Md, No, and Lr. These elements are used for catalyst preparation singly or as a mixture of two or more of them.

Preferable examples of the metal oxide composition (B) include CuO, CuO—ZnO, CuO—ZnO—BaO, CuO—ZnO—MgO, CuO—ZnO—CaO, CuO—ZnO—$Y_2O_3$, CuO—ZnO—$La_2O_3$, CuO—ZnO—$ThO_2$, CuO—BaO, CuO—MgO, CuO—CaO, CuO—$Y_2O_3$, and CuO—$La_2O_3$.

In this invention, for elongation of the catalyst life, tungsten oxide ($WO_3$) and/or molybdenum oxide ($MoO_3$) may be added to the metal oxide composition as proposed by the present inventors in Japanese Unexamined Patent Publication No.3-220143.

Although the method of applying the metal oxide composition (B) onto the catalyst carrier (A) or mixing the both is not particularly limited, the methods proposed in Japanese Unexamined Patent Publication No.1-305042 are preferred.

Specifically, the metal oxide composition (B) may be applied onto the catalyst carrier (A) by any one of the following methods to obtain the catalyst precursor of the present invention:

(1) a precipitating agent is added to a metal salt solution, i.e., a solution of catalyst components other than the catalyst carrier (A), in the presence of the catalyst carrier (A), and the resulting coprecipitate is washed with water, dried and calcinated (coprecipitation method);

(2) the catalyst carrier (A) is impregnated with the metal salt solution, i.e., a solution of catalyst components other than the catalyst carrier (A), dried and calcinated (impregnation method); and (3) the catalyst carrier (A) is uniformly mixed with compounds such as an oxide, a hydroxide and a carbonate of the metals which constitute the metal oxide composition (B), and the mixture is calcinated (mixing method).

The catalyst precursor prepared by the coprecipitation method or by the impregnation method has the metal oxide composition (B) uniformly distributed and carried on the surface of the catalyst carrier (A), while the catalyst precursor prepared by the mixing method has the metal oxide composition (B) spottedly adhered to the surface of the catalyst carrier (A). Therefore, in view of efficient utilization of the catalytically active metal components, a preference is given to the coprecipitation and impregnation methods.

The metal salts used in the above coprecipitation and impregnation methods may be any water soluble salts. A sulfate, nitrate, ammonium complex salt, acetate, oxalate, acetyl acetonate and chloride are usually used as the metal salts of copper, zinc, elements of group IIa, elements of group IIIb, lanthanide elements and actinide elements.

Examples of precipitating agents used in the above coprecipitation method include alkaline solutions such as solutions of ammonia, urea, ammonium carbonate, sodium carbonate, sodium bicarbonate, sodium hydroxide and potassium hydroxide. When the catalyst precursor of the present invention is prepared by the coprecipitation method, adjustment of pH is important. The coprecipitation method is performed preferably at a pH of from 2 to 11.

In the methods described above, burning is carried out preferably at a temperature of from 300° to 600 ° C. in an oxidizing atmosphere.

In order to increase the catalyst strength, the catalyst precursor may further contain a slight amount of the following substances to the extent that they do not impair the advantageous effect of the present invention: graphite, fatty acid salts, starch, mineral oil, talc, bentonite, and alkali metals.

The catalyst precursor thus obtained may be used in the form of a powder, and it may also be used in the form of tablets by molding the powder into tablets.

2. Reduction of the Catalyst Precursor

The catalyst precursor thus obtained is reduced to obtain a hydrogenation reaction catalyst, and the hydrogenation reaction catalyst obtained is used for producing, for example, an alcohol by hydrogenating an organic carboxylic acid ester.

The above reductive activation of the catalyst precursor may employ either a vapor-phase reduction or a liquid-phase reduction which is carried out in a hydrocarbon (e.g. paraffin) or in a solvent such as dioxane, an aliphatic alcohol and a fatty acid ester.

For example, when the catalyst precursor is reduced using hydrogen gas, it is preferred to carry out the reduction at a temperature of from 100° to 800° C., preferably from 150° to 500° C., until the formation of water or the absorption of hydrogen is not observed. When the reduction is carried out in a solvent, it is preferred to carry out the reduction at a temperature of from 150° to 350° C. until the absorption of hydrogen is not observed. An ordinary reductive activation method may be used without any problems, wherein the catalyst precursor is reduced in an organic carboxylic acid ester, which is the raw material of alcohol production, at a raised temperature in a hydrogen reducing atmosphere, and the resulting catalyst is directly used for the hydrogenation reaction to produce an alcohol.

Reducing agents which can be used for reducing the catalyst precursor of the present invention include hydrogen, carbon monoxide, ammonia, hydrazine, formaldehyde, and a lower alcohol such as methanol. These reducing agents may be used singly or as a mixture of two or more of them. Also, these reducing agents can be used after being diluted with an inert gas such as nitrogen, helium, argon, or in the presence of a small amount of steam.

By the above reduction, the copper oxide in the catalyst precursor of the present invention is reduced to a catalytically active reduced copper. An X-ray diffraction analysis reveals that the other components of the catalyst precursor remain almost unchanged without undergoing any substantial reduction.

By the use of the hydrogenation reaction catalyst obtained by the above processes, an organic carboxylic acid ester can be catalytically hydrogenated with hydrogen to a corresponding alcohol at a practical reaction rate even though the reaction is carried out at a low reaction temperature and a low hydrogen pressure, and an alcohol of high quality is produced at a high yield and with a high selectivity. The catalyst according to the present invention has a practical use in a large-scale industrial production, because it can be produced at a low cost using a less expensive carrier base material than titanium oxide and/or titanium hydroxide. Moreover, the catalyst of the present invention is superior to those using a titanium oxide and/or titanium hydroxide carrier base material in catalytic activity and reaction selectivity.

3. Process for Production of Alcohol

The process for producing an alcohol in the present invention is characterized by catalytically hydrogenating an organic carboxylic acid ester with hydrogen in the presence of the hydrogenation reaction catalyst which can be obtained by reducing the catalyst precursor prepared by the above-mentioned processes. In the catalytic hydrogenation of an organic carboxylic acid ester, the carboxylic acid moiety is reduced to form a corresponding alcohol.

The organic carboxylic acid esters used as raw materials for producing alcohols in the present invention include esters formed between a saturated or unsaturated aliphatic carboxylic acid having a straight or branched chain of 1 or more carbon atoms and a lower or higher alcohol, and esters formed between an alicyclic carboxylic acid or an aromatic carboxylic acid and a lower or higher alcohol. There is no particular limitation on the alcohol moiety constituting the carboxylic acid ester. Examples of the organic carboxylic acid esters used in the present invention include formic acid esters, acetic acid esters, caproic acid esters, caprylic acid esters, undecenic acid esters, lauric acid esters, myristic acid esters, palmitic acid esters, stearic acid esters, isostearic acid esters, oleic acid esters, oxalic acid esters, maleic acid esters, adipic acid esters, sebacic acid esters, cyclohexanecarboxylic acid esters, benzoic acid esters, and phthalic acid esters.

The above carboxylic acid esters may be hydrogenated by a suspensoid bed reaction system, a fixed bed reaction system or a fluid bed reaction system. Depending upon the systems used, the form of the catalyst may be changed.

For example, when the suspensoid bed reaction system is employed, the catalyst in the form of powder is used. It is possible to conduct the reaction in the presence of a solvent which does not give adverse effect on the hydrogenation reaction. Solvents such as an alcohol, dioxane and hydrocarbon may be used. However, in view of productivity, the hydrogenation reaction should preferably be carried out in the absence of such a solvent. In this system, the amount of the catalyst is preferably from 0.1 to 20 parts by weight, based on 100 parts by weight of the carboxylic acid ester. However, depending upon the reaction temperature and pressure, it can be optionally determined within the range where a practical reaction rate can be achieved. The reaction temperature is from 160° to 350° C., preferably from 180° to 280° C. The reaction pressure is from 1 to 350 kg/cm$^2$, preferably from 30 to 300 kg/cm$^2$.

When a fixed bed reaction system is employed, the catalyst which is molded to suit a specific purpose may be used. In this system, the reaction temperature is from 130° to 300° C., preferably from 160° to 270° C., and the reaction pressure is from 0.1 to 300 kg/cm$^2$. The liquid hourly space velocity (LHSV) is optionally determined according to reaction conditions. It is preferably in the range of from 0.5 to 5 in view of productivity and catalyst reactivity.

The invention will now be described in more detail by the following examples, but it should be noted that the invention is not limited to these examples.

EXAMPLES

Example 1

Preparation of catalyst precursor

γ-alumina (A-II with surface area of 120 m$^2$/g, manufactured by Nishio Kogyo Co., Ltd.), a carrier base material, is suspended in isopropyl alcohol, to which tetraisopropyl titanate $\{[(CH_3)_2CHO]_4Ti\}$ is added in an amount of 20 parts by weight, as calculated as titanium oxide, based on 100 parts by weight of the base material, and sufficiently stirred. Then, water is added in an adequate amount for hydrolysis with stirring at a room temperature to form a titanium hydroxide coating on the surface of the carrier base material. After the completion of hydrolysis, the isopropyl alcohol in the system is distilled off. To the residue (carrier component), an aqueous mixture of copper nitrate and zinc nitrate and an aqueous solution of 10% by weight sodium carbonate are added and mixed with stirring at 98° C. to obtain a slurry having a pH of 9 of a catalyst precursor. The precipitate is separated from the slurry by filtration, sufficiently washed with water and dried to obtain the catalyst precursor of the present invention. The catalyst precursor obtained has the following weight composition:

CuO:ZnO:Carrier Component=38%:2%:60%

(CuO:ZnO=1:0.05 by weight)
The weight composition of the carrier component is:

γ-Al$_2$O$_3$:TiO$_2$=83.3%:16.7%

(Coating: 20%)

The powder of the catalyst precursor thus obtained is formed into tablets having a diameter of 3 mm. After the tablets are calcinated in the air atmosphere at a temperature of 450° C. for 2 hours, the catalytic activity and the reaction selectivity are evaluated in the manner as mentioned below.

Evaluation of catalytic activity and reaction selectivity

Fifteen grams of the catalyst precursor tablets obtained in the above process is placed in an autoclave-type basket reactor together with 200 g of lauryl alcohol, and subjected to reductive activation which is carried out at a hydrogen pressure of 10 kg/cm$^2$ (gauge pressure) and a temperature of 200° C. for 2 hours under a hydrogen stream. After the completion of the reduction, lauryl alcohol is replaced with 200 g of a palm kernel fatty acid methyl ester [saponification value (SV)=250 mg KOH/g], and the reduction is carried out at a hydrogen pressure of 120 kg/cm$^2$ (gauge pressure) and a temperature of 230° C. in a hydrogen stream with stirring at 900 rpm, during which the SV value is determined at several time points to calculate the primary reaction rate constant k. The k value is used as an index of the catalytic activity.

Also, the samples taken at several time points during the reaction are analyzed with capillary gas chromatography to obtain the contents (%) of methyl ether and hydrocarbon when the saponification value (SV) is 10 mg KOH/g. The contents are used as the indices for the reaction selectivity of the catalyst. The results are shown in Table 1.

Example 2

The same γ-alumina as used in Example 1, the carrier base material, is suspended in isopropyl alcohol, to which tetraisopropyl titanate $\{[(CH_3)_2CHO]_4Ti\}$ is added in an amount of 10 parts by weight, as calculated as titanium oxide, based on 100 parts by weight of the base material, and a coating of titanium hydroxide is formed on the surface of the base material by hydrolysis. Then, by the same procedures as in Example 1, a tableted catalyst precursor is obtained. The catalyst precursor thus obtained is evaluated for the catalytic activity and the reaction selectivity in the same manner as in Example 1. The results are shown in Table 1.

Example 3

The same γ-alumina as used in Example 1, the carrier base material, is suspended in isopropyl alcohol, to which tetraisopropyl titanate $\{[(CH_3)_2CHO]_4Ti\}$ is added in an amount of 5 parts by weight, as calculated as titanium oxide, based on 100 parts by weight of the carrier base material, and a coating of titanium hydroxide is formed on the surface of the carrier base material by hydrolysis. Then, by the same procedures as in Example 1, a tableted catalyst precursor is obtained. The catalyst precursor thus obtained is evaluated for the catalytic activity and the reaction selectivity in the same manner as in Example 1. The results are shown in Table 1.

Comparative Example 1

The same γ-alumina as used in Example 1 is used as the carrier base material without the coating treatment with titanium oxide. That is, to an aqueous suspension of the carrier base material, an aqueous mixture of copper nitrate and zinc nitrate and an aqueous solution of 10% by weight sodium carbonate are added and mixed with stirring at 98° C. to obtain a slurry having a pH of 9. The precipitate is separated from the slurry by filtration, sufficiently washed with water, and dried, and then calcinated at 450° C. for 2 hours to obtain a catalyst precursor where copper oxide-zinc oxide is carried on γ-alumina. The resulting catalyst precursor has the following weight composition:

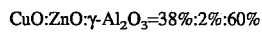

$CuO:ZnO:\gamma\text{-}Al_2O_3 = 38\%:2\%:60\%$

The catalyst precursor thus obtained is evaluated for the catalytic activity and the reaction selectivity in the same manner as in Example 1. The results are shown in Table 1.

Example 4

The same γ-alumina as used in Example 1, the carrier base material, is calcinated at 1000° C. for 2 hours in an oxidizing atmosphere to obtain an alumina powder having a surface area of 40 m²/g. This alumina powder is suspended in isopropyl alcohol, to which tetraisopropyl titanate is added in an amount of 10 parts by weight, as calculated as titanium oxide, based upon 100 parts by weight of the carrier base material to form a coating of titanium hydroxide on the surface of the carrier base material by hydrolysis. Then, by following the same procedures as in Example 1, a catalyst precursor is obtained. The catalyst precursor thus obtained is evaluated for the catalytic activity and the reaction selectivity in the same manner as in Example 1. The results are shown in Table 1.

The results of Examples 1 to 4 and Comparative Example 1 in Table 1 reveal that the amount of the coating titanium oxide/hydroxide and the surface area of the base material have significant influences on the catalytic activity and the reaction selectivity.

Comparative Examples 2 and 3

Catalyst precursors are prepared by following the same procedures as in Example 1 except that the ratio of copper nitrate to zinc nitrate and the amount of the carrier base material are changed. The catalyst precursors thus obtained are evaluated for the catalytic activity and the reaction selectivity in the same manner as in Example 1. The results are shown in Table 1.

The results of Comparative Examples 2 and 3 show that when the ratio of copper oxide to zinc oxide or the ratio of the carrier base material (A) to the metal oxide composition (B) is not within the claimed range, the desired catalytic activity and reaction selectivity cannot be obtained.

Example 5

γ-alumina (with a surface area of 150 m²/g, manufactured by Sakai Chemical Industry Co., Ltd.), a carrier base material, is suspended in isopropyl alcohol, to which tetraisopropyl titanate is added in an amount of 10 parts by weight, as calculated as titanium oxide, based on 100 parts by weight of the carrier base material, and a coating of titanium hydroxide is formed on the surface of the carrier base material by hydrolysis. Then, by the same procedures as in Example 1, a tableted catalyst precursor is obtained. The catalyst precursor thus obtained is evaluated for the catalytic activity and the reaction selectivity in the same manner as in Example 1. The results are shown in Table 1.

Comparative Example 4

A catalyst precursor is prepared according to the process proposed by the inventors in Japanese Unexamined Patent Publication No. 5-177140 (U.S. Pat. No. 5,229,346) using a commercially available titanium oxide having a large surface area (with a surface area of 150 m²/g, manufactured by Sakai Chemical Industry Co., Ltd.) as a carrier base material. The catalyst precursor thus obtained is evaluated for the catalytic activity and the reaction selectivity in the same manner as in Example 1. The results are shown in Table 1.

As is clear from the results of Comparative Example 4, the catalyst precursor of the present invention provides a higher catalytic activity and reaction selectivity than the catalyst precursor proposed by the inventors in the above publication.

TABLE 1

| | Catalyst precursor composition (weight ratio) | Catalyst carrier (A) | | | Reaction Evaluation | | |
|---|---|---|---|---|---|---|---|
| | | Carrier base material | | | Rate constant $k^{*3}$ ($Hr^{-1}$) | Selectivity*4 | |
| | | Material | Surface area*1 ($m^2/g$) | Amount of $TiO_2$ coating*2 | | Hydrocarbon content (%) | Methyl ether content (%) |
| Example 1 | CuO:ZnO:Catalyst carrier (A) = 38%:2%:60% (CuO:ZnO = 1:0.05) | γ-Alumina (γ-$Al_2O_3$) | 120 | 20 | 1.0 | 0.06 | 0.09 |
| Example 2 | CuO:ZnO:Catalyst carrier (A) = 38%:2%:60% (CuO:ZnO = 1:0.05) | γ-Alumina (γ-$Al_2O_3$) | 120 | 10 | 1.3 | 0.06 | 0.09 |
| Example 3 | CuO:ZnO:Catalyst carrier (A) = 38%:2%:60% (CuO:ZnO = 1:0.05) | γ-Alumina (γ-$Al_2O_3$) | 120 | 5 | 1.0 | 0.08 | 0.09 |
| Comparative | CuO:ZnO:Catalyst carrier (A) = 38%:2%:60% | γ-Alumina (γ-$Al_2O_3$) | 120 | 0 | 0.2 | 0.23 | 0.15 |

TABLE 1-continued

| | Catalyst precursor composition (weight ratio) | Catalyst carrier (A) Carrier base material | | | Reaction Evaluation | | |
|---|---|---|---|---|---|---|---|
| | | Material | Surface area*1 (m²/g) | Amount of TiO₂ coating*2 | Rate constant k*3 (Hr⁻¹) | Selectivity*4 Hydrocarbon content (%) | Methyl ether content (%) |
| Example 1 | (CuO:ZnO = 1:0.05) | | | | | | |
| Example 4 | CuO:ZnO:Catalyst carrier (A) = 38%:2%:60% (CuO:ZnO = 1:0.05) | γ-Alumina (γ-Al₂O₃) | 40 | 10 | 0.7 | 0.06 | 0.08 |
| Comparative Example 2 | CuO:ZnO:Catalyst carrier (A) = 31%:9%:60% (CuO:ZnO = 1:0.29) | γ-Alumina (γ-Al₂O₃) | 120 | 10 | 0.3 | 0.06 | 0.10 |
| Comparative Example 3 | CuO:ZnO:Catalyst carrier (A) = 76%:4%:20% (CuO:ZnO = 1:0.05) | γ-Alumina (γ-Al₂O₃) | 120 | 10 | 0.2 | 0.06 | 0.10 |
| Example 5 | CuO:ZnO:Catalyst carrier (A) = 38%:2%:60% (CuO:ZnO = 1:0.05) | γ-Alumina (γ-Al₂O₃) | 150 | 10 | 1.4 | 0.06 | 0.09 |
| Comparative Example 4 | CuO:ZnO:Catalyst carrier (A) = 38%:2%:60% (CuO:ZnO = 1:0.05) | Titania (TiO₂) | 150 | 10 | 1.0 | 0.12 | 0.10 |

*1 The surface area is measured by the BET method.
*2 Parts by weight, based on 100 parts by weight of a carrier base material.
*3 The larger the value is, the higher the activity.
*4 The smaller the value is, the higher the selectivity.
The same notes as above are applied also to Tables 2 and 3.

Examples 6 to 9

The molded catalyst precursors are prepared by following the same procedures as in Example 2 except that type 3A zeolite (Zeolam A-3™ with a surface area of 800 m²/g, manufactured by Toyo Soda Manufacturing Co., Ltd.), silica-alumina (Kyoward 700™ with a surface area of 540 m²/g, manufactured by Kyowa Chemical Industry, Co., Ltd.), silica (P-78D™ with a surface area of 350 m²/g, manufactured by Mizusawa Industrial Chemicals, Co., Ltd.) or zirconia (with a surface area of 150 m²/g, manufactured by Daiichikigenso Industrial Chemicals Co., Ltd.) is used instead of γ-alumina as the carrier base material. The thus-obtained catalyst precursors are evaluated for the catalytic activity and the reaction selectivity in the same manner as in Example 1. The results are shown in Table 2.

Comparative Examples 5 to 8

The molded catalyst precursors of Comparative Examples 5 to 8 are obtained by respectively following the same procedures as in Examples 6 to 9 except that the coating treatment with titanium hydroxide is omitted. The catalyst precursors thus obtained are evaluated for the catalytic activity and the reaction selectivity in the same manner as in Example 1. The results are shown in Table 2.

TABLE 2

| | Catalyst precursor composition (weight ratio) | Catalyst carrier (A) Carrier base material | | | Reaction Evaluation | | |
|---|---|---|---|---|---|---|---|
| | | Material | Surface area*1 (m²/g) | Amount of TiO₂ coating*2 | Rate constant k*3 (Hr⁻¹) | Selectivity*4 Hydrocarbon content (%) | Methyl ether content (%) |
| Example 6 | CuO:ZnO:Catalyst carrier (A) = 38%:2%:60% (CuO:ZnO = 1:0.05) | Type 3A Zeolite | 800 | 10 | 1.2 | 0.05 | 0.09 |
| Comparative Example 5 | CuO:ZnO:Catalyst carrier (A) = 38%:2%:60% (CuO:ZnO = 1:0.05) | Type 3A Zeolite | 800 | 0 | 0.5 | 0.20 | 0.17 |
| Example 7 | CuO:ZnO:Catalyst carrier (A) = | Silica- | 540 | 10 | 1.1 | 0.06 | 0.09 |

TABLE 2-continued

| | Catalyst precursor composition (weight ratio) | Catalyst carrier (A) | | | Reaction Evaluation | | |
|---|---|---|---|---|---|---|---|
| | | Carrier base material | | | Rate con- stant k*[3] (Hr$^{-1}$) | Selectivity*[4] | |
| | | Material | Surface area*[1] (m$^2$/g) | Amount of TiO$_2$ coating*[2] | | Hydro- carbon content (%) | Methyl ether content (%) |
| | 38%:2%:60% (CuO:ZnO = 1:0.05) | alumina | | | | | |
| Comparative Example 6 | CuO:ZnO:Catalyst carrier (A) = 38%:2%:60% (CuO:ZnO = 1:0.05) | Silica- alumina | 540 | 0 | 0.4 | 0.21 | 0.15 |
| Example 8 | CuO:ZnO:Catalyst carrier (A) = 38%:2%:60% (CuO:ZnO = 1:0.05) | Silica (SiO$_2$) | 350 | 10 | 1.2 | 0.06 | 0.09 |
| Comparative Example 7 | CuO:ZnO:Catalyst carrier (A) = 38%:2%:60% (CuO:ZnO = 1:0.05) | Silica (SiO$_2$) | 350 | 0 | 0.2 | 0.22 | 0.16 |
| Example 9 | CuO:ZnO:Catalyst carrier (A) = 38%:2%:60% (CuO:ZnO = 1:0.05) | Zirconia (ZrO$_2$) | 150 | 10 | 1.1 | 0.06 | 0.08 |
| Comparative Example 8 | CuO:ZnO:Catalyst carrier (A) = 38%:2%:60% (CuO:ZnO = 1:0.05) | Zirconia (ZrO$_2$) | 150 | 0 | 0.3 | 0.21 | 0.16 |

By comparing the results of Examples 6 to 9 with those of Comparative Examples 5 to 8, it is found that catalyst precursors prepared by the process of the present invention are higher in the catalytic activity and the reaction selectivity than those prepared without the coating treatment with titanium hydroxide whichever material mentioned above may be used as the carrier base material.

Example 10

A molded catalyst precursor is prepared by the same procedures as in Example 2 except that barium nitrate is added in addition to copper nitrate and zinc nitrate. The catalyst precursor thus obtained is evaluated for the catalytic activity and the reaction selectivity in the same manner as in Example 1. The results are shown in Table 3.

Comparative Example 9

A molded catalyst precursor is prepared by the same procedures as in Example 10 except that the amount of barium nitrate is changed. The catalyst precursor thus obtained is evaluated for the catalytic activity and the reaction selectivity in the same manner as in Example 1. The results are shown in Table 3.

Examples 11 to 13

Molded catalyst precursors are obtained by the same procedures as in Example 10 except that nitrates of Y of group IIIb, La of the lanthanide group and Th of the actinide group are used in place of the nitrate of Ba of group IIa (i.e. barium nitrate), respectively in Examples 11 to 13. The catalyst precursors thus obtained are evaluated for the catalytic activity and the reaction selectivity in the same manner as in Example 1. The results are shown in Table 3.

TABLE 3

| | Catalyst precursor composition (weight ratio) | Catalyst carrier (A) | | | Reaction Evaluation | | |
|---|---|---|---|---|---|---|---|
| | | Carrier base material | | | Rate con- stant k*[3] (Hr$^{-1}$) | Selectivity*[4] | |
| | | Material | Surface area*[1] (m$^2$/g) | Amount of TiO$_2$ coating*[2] | | Hydro- carbon content (%) | Methyl ether content (%) |
| Example 10 | CuO:ZnO:BaO:Catalyst carrier (A) = 33.7%:2.7%:3.3%:60.3% (CuO:ZnO:BaO = 1:0.08:0.10) | γ-Alumina | 120 | 10 | 1.2 | 0.06 | 0.04 |
| Comparative Example 9 | CuO:ZnO:BaO:Catalyst carrier (A) = 31.5%:2.6%:9.5%:56.4% (CuO:ZnO:BaO = 1:0.08:0.30) | γ-Alumina | 120 | 10 | 0.5 | 0.06 | 0.04 |

TABLE 3-continued

| | Catalyst precursor composition (weight ratio) | Catalyst carrier (A) | | | Reaction Evaluation | | |
|---|---|---|---|---|---|---|---|
| | | Carrier base material | | | Rate constant k*[3] (Hr$^{-1}$) | Selectivity*[4] | |
| | | Material | Surface area*[1] (m$^2$/g) | Amount of TiO$_2$ coating*[2] | | Hydrocarbon content (%) | Methyl ether content (%) |
| Example 11 | CuO:ZnO:Y$_2$O$_3$:Catalyst carrier (A) = 33.7%:2.7%:3.3%:60.3% (CuO:ZnO:Y$_2$O$_3$ = 1:0.08:0.10) | γ-Alumina | 120 | 10 | 1.2 | 0.06 | 0.03 |
| Example 12 | CuO:ZnO:La$_2$O$_3$:Catalyst carrier (A) = 33.7%:2.7%:3.3%:60.3% (CuO:ZnO:La$_2$O$_3$ = 1:0.08:0.10) | γ-Alumina | 120 | 10 | 1.1 | 0.06 | 0.03 |
| Example 13 | CuO:ZnO:ThO$_2$:Catalyst carrier (A) = 33.7%:2.7%:3.3%:60.3% (CuO:ZnO:ThO$_2$ = 1:0.08:0.10) | γ-Alumina | 120 | 10 | 1.2 | 0.06 | 0.03 |

By comparing the results of Example 10 with those of Comparative Example 9, it is found that when the weight ratio of the metal oxide composition is outside the claimed range, desired activity cannot be obtained.

The results of Examples 11 to 13 show that the third metal oxide component can be changed within the claimed group without impairing the excellent catalytic activity and the reaction selectivity of the catalyst precursor of the present invention.

While the invention has been described in detail and with reference to specific embodiments thereof, it will be apparent to one skilled in the art that various changes and modifications can be made therein without departing from the spirit and scope thereof.

What is claimed is:

1. A hydrogenation reaction catalyst precursor comprising a catalyst carrier (A) and a metal oxide composition (B) carried on or mixed with the catalyst carrier (A) at a weight ratio of (B)/(A)=15/85 to 65/35, wherein the catalyst carrier (A) comprises a carrier base material of at least one kind selected from the group consisting of silica, alumina, silica-alumina, magnesia, zirconia, zeolite, and diatomaceous earth, said carrier base material being coated with titanium oxide and/or titanium hydroxide; and wherein the metal oxide composition (B) comprises copper oxide, zinc oxide, and at least one oxide of a metal selected from the group consisting of an element of group IIa of the periodic table, an element of group IIIb of the periodic table, a lanthanide element, and an actinide element at a weight ratio of 100/(0 to 25)/(0 to 25).

2. The hydrogenation reaction catalyst precursor according to claim 1, wherein said carrier base material is coated with the titanium oxide and/or titanium hydroxide at a weight ratio of the titanium oxide and/or hydroxide to the carrier base material being 5/100 to 100/100.

3. The hydrogenation reaction catalyst precursor according to claim 1, wherein said carrier base material has a surface area of not less than 15 m$^2$/g.

4. The hydrogenation reaction catalyst precursor according to claim 1, wherein said metal oxide composition (B) is selected from the group consisting of CuO, CuO—ZnO, CuO—ZnO—BaO, CuO—ZnO—MgO, CuO—ZnO—CaO, CuO—ZnO—Y$_2$O$_3$, CuO—ZnO—La$_2$O$_3$, CuO—ZnO—ThO$_2$, CuO—BaO, CuO—MgO, CuO—CaO, CuO—Y$_2$O$_3$, and CuO—La$_2$O$_3$.

5. A process for producing a hydrogenation reaction catalyst precursor, comprising the steps of:

(i) coating a surface of a carrier base material of at least one kind selected from the group consisting of silica, alumina, silica-alumina, magnesia, zirconia, zeolite, and diatomaceous earth with a titanium oxide and/or titanium hydroxide to give a catalyst carrier (A); and (ii) applying a metal oxide composition (B) onto the catalyst carrier (A) obtained in step (i) or mixing the metal oxide composition (B) with the catalyst carrier (A) at a weight ratio of (B)/(A)=15/85 to 65/35 to obtain a hydrogenation reaction catalyst precursor, wherein the metal oxide composition (B) comprises copper oxide, zinc oxide, and at least one oxide of a metal selected from the group consisting of an element of group IIa of the periodic table, an element of group IIIb of the periodic table, a lanthanide element, and an actinide element at a weight ratio of 100/(0 to 25)/(0 to 25), and wherein the catalyst carrier (A) may be or may not be calcinated.

6. The process according to claim 5, wherein the amount of the titanium oxide and/or titanium hydroxide to the carrier base material is 5/100 to 100/100 by weight.

7. The process according to claim 5, wherein said carrier base material has a surface area of not less than 15 m$^2$/g.

8. The process according to claim 5, wherein the coating in the step (i) is carried out by forming a titanium oxide and/or titanium hydroxide in the presence of the carrier base material by hydrolyzing at least one of a titanium alkoxide represented by the following Formula (I) and a titanium alkoxo acid represented by the following Formula (II):

$$Ti(OR)_4 \qquad (I)$$

wherein R represents an alkyl group having from 1 to 18 carbon atoms or aryl group, and $$H_2[Ti(OR)_6] \qquad (II)$$

wherein R has the same meaning as above.

9. A hydrogenation reaction catalyst obtained by reducing the hydrogenation reaction catalyst precursor of claim 1.

10. The hydrogenation reaction catalyst according to claim 9, wherein the hydrogenation reaction catalyst precursor is reduced with hydrogen gas at a temperature of from 100° to 800° C.

11. The hydrogenation reaction catalyst according to claim 9, wherein the hydrogenation reaction catalyst precursor is reduced in a solvent at a temperature of from 150° to 350° C.

12. The hydrogenation reaction catalyst according to claim 9, wherein the hydrogenation reaction catalyst precursor is reduced in an organic carboxylic acid ester.

13. A process for producing an alcohol, comprising a step of catalytically hydrogenating an organic carboxylic acid ester with hydrogen in the presence of the hydrogenation reaction catalyst of claim 9.

14. The process according to claim 13, wherein the organic carboxylic acid ester is an ester formed between a saturated or unsaturated aliphatic carboxylic acid having a straight or branched chain of 1 or more carbon atoms and an alcohol, or an ester formed between an alicyclic carboxylic acid or an aromatic carboxylic acid and an alcohol.

15. The process according to claim 5, wherein step (ii) is carried out by:

(1) a coprecipitation method wherein the metal oxide composition (B) is coprecipitated with the catalyst carrier (A) in a metal salt solution of copper and at least one metal selected from the group consisting of zinc, an element of group IIa of the periodic table, an element of group IIIb of the periodic table, a lanthanide element and an actinide element; or (2) an impregnation method wherein the catalyst carrier (A) is impregnated with a metal salt solution of copper and at least one metal selected from the group consisting of zinc, an element of group IIa of the periodic table, an element of group IIIb of the periodic table, a lanthanide element and an actinide element.

* * * * *